United States Patent [19]

Merz et al.

[11] 4,039,576
[45] Aug. 2, 1977

[54] PROCESS FOR THE MANUFACTURE OF ALKOXYLATED N-METHYLOL UREAS

[75] Inventors: Jurg Merz, Therwil; Luzius Schibler, Riehen, both of Switzerland

[73] Assignee: Ciba-Geigy Corporation, Ardsley, N.Y.

[21] Appl. No.: 635,530

[22] Filed: Nov. 26, 1975

Related U.S. Application Data

[62] Division of Ser. No. 344,669, March 26, 1973, Pat. No. 4,013,655.

[30] Foreign Application Priority Data

Mar. 28, 1972 Switzerland .................... 4632/72

[51] Int. Cl.$^2$ ............... C07C 127/15; C07C 127/17; C07C 127/19
[52] U.S. Cl. ................ 260/553 R; 260/553 A; 260/558 R; 260/558 D; 260/559 R; 260/561 R; 260/561 N; 252/461; 252/467; 252/476
[58] Field of Search .................... 260/553 R, 553 A; 252/467, 461, 476

[56] References Cited

U.S. PATENT DOCUMENTS

| | | | |
|---|---|---|---|
| 2,059,273 | 11/1936 | Piggott | 260/553 R X |
| 2,123,718 | 7/1938 | De Groote | 260/553 R X |
| 2,155,328 | 4/1939 | Paquin | 260/553 R X |
| 2,674,619 | 4/1954 | Lundsted | 260/553 R X |
| 2,892,810 | 6/1959 | Albrecht | 260/249.6 X |
| 3,179,667 | 4/1965 | Walles | 260/553 R X |
| 3,377,316 | 4/1968 | Reinking et al. | 260/553 R X |
| 3,397,178 | 8/1968 | Shackelford et al. | 260/553 R X |
| 3,927,089 | 12/1975 | Schibler et al. | 260/553 R |

OTHER PUBLICATIONS

Ciba Ltd., CA 58:P12701b (1963).
Bradley et al., CA 52:6049e (1958).
Thomas, CA 55:24542f (1961).

*Primary Examiner*—Daniel E. Wyman
*Assistant Examiner*—Thomas A. Waltz
*Attorney, Agent, or Firm*—Karl F. Jorda; Edward McC. Roberts; Prabodh I. Almaula

[57] ABSTRACT

A new process for the manufacture of alkoxylated N-methylol compounds, which comprises reacting a. a N-methylolated organic nitrogen compound with b. an alkylene oxide of the formula

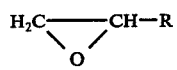

wherein R denotes hydrogen, alkyl with 1 to 3 carbon atoms, phenyl or a

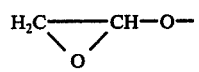

radical, in the presence of c. at least one metal alcoholate of the formula

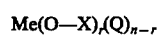

wherein Me denotes a n-valent transition metal of groups IV, V or VI of the periodic system, X denotes alkyl with 1 to 4 carbon atoms, halogenoalkyl with 2 to 4 carbon atoms, phenyl, benzyl or cycloalkyl with at most 12 ring carbon atoms, Q denotes halogen or alkoxy with 1 to 4 carbon atoms, r denotes 1 to n and n denotes 4, 5 or 6, or in the present of said component (c) together with (d) at least one alkali metal hydroxide or one alkali metal alcoholate of an alkanol with 1 to 4 carbon atoms, at a temperature of 10° to 160° C and a pressure of 1 to 20 atmospheres gauge.

13 Claims, No Drawings

PROCESS FOR THE MANUFACTURE OF ALKOXYLATED N-METHYLOL UREAS

This is a divisional of application Ser. No. 344,669, filed on Mar. 26, 1973, now U.S. Pat. No. 4,013,655.

The invention relates to a process for the manufacture of alkoxylated N-methylol compounds, characterised in that a. a N-methylolated organic nitrogen compound is reacted with b. an alkylene oxide of the formula

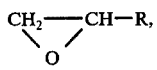 (1)

wherein R denotes phenyl, alkyl with 1 to 3 carbon atoms, a

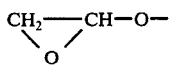

radical or, preferably, hydrogen, in the presence of c. at least one metal alcoholate of the formula 2. $Me(O-X)_r(Q)_{n-r}$ wherein Me denotes a $n$-valent transition metal of groups IV, V or VI of the periodic system, X denotes phenyl, benzyl, cycloalkyl with at most 12, especially 5 to 12, and above all 8 to 12, ring carbon atoms, halogenoalkyl with 2 to 4 carbon atoms, or preferably, alkyl with 1 to 4 carbon atoms, Q denotes halogen or alkoxy with 1 to 4 carbon atoms, $r$ denotes 1 to $n$ and $n$ denotes 4, 5 or 6, and optionally (d) at least one alkali metal hydroxide or one alkali metal alcoholate of an alkanol with 1 to 4 carbon atoms, at a temperature of 10° to 160° C and a pressure of 1 to 20 atmospheres gauge.

The components (a) are as a rule addition products of formaldehyde to nitrogen compounds which can be methylolated such as, for example, urea or thiourea compounds, 1,3,5-aminotriazines or carboxylic acid amides.

Examples of suitable urea and thiourea compounds are urea, thiourea, substituted ureas such as alkylureas and arylureas, alkyleneureas and alkylenediureas, such as ethyleneurea propyleneurea, dihydroxyethyleneurea, hydroxypropyleneurea and acetylenediurea, and also dicyandiamide, dicyandiamidine, urones and hexahydropyrimidones.

As examples of 1,3,5-aminotriazines there may be mentioned: melamine and N-substituted melamines, such as N-butylmelamine, N-trihalogenomethylmelamines, triazones, ammeline, guanamines, for example benzoguanamines and acetoguanamines, or diguanamines.

In general, products which are as highly methylolated as possible yield particularly valuable products. Partial ethers of such methylol compounds with, for example, alkanols with 1 to 22 carbon atoms, such as methanol, ethanol, n-propanol, isopropanol, n-butanol or octadecyl alcohol can also be used.

The N-methylolated carboxylic acid amides are, for example, amides of aromatic or aliphatic carboxylic acids, such as benzoic acids optionally substituted by lower alkyl, lower alkoxy, hydroxyl or halogen, or, preferably, amides of saturated or unsaturated aliphatic carboxylic acids. Particularly suitable compounds of this nature are N-methylolated aliphatic carboxylic acid amides with at most 22 carbon atoms, above all N-methylolated alkylmonocarboxylic acid amides or alkenylmonocarboxylic acid amides with 3 to 22, preferably 10 to 18, carbon atoms. As examples, the mono- or di-N-methylolated amides of, for example, stearic acids, palmitic acid, lauric acid, hydroabietic acid, oleic acid, linoleic acid, linolenic acid, caprylic acid, butyric acid, acrylic acid and methacrylic acid may be mentioned here.

Preferably, N-methylolated 1,3,5-aminotriazines, ureas or aliphatic carboxylic acid amides with at most 22 carbon atoms are used as component (a) in the process according to the invention. Amongst these components, N-methylolmelamines and N-methylolureas are of great practical interest.

Compounds of the formula

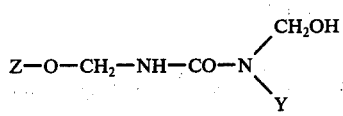 (3)

wherein Y denotes alkyl with 1 to 4 carbon atoms or, preferably, hydrogen or methylol and Z denotes alkyl with 1 to 22 carbon atoms, alkenyl with 3 to 22 carbon atoms, a monoalkylene glycol or polyalkylene glycol radical with 2 or 3 carbon atoms per alkylene unit and with up to 100 alkoxy groups in the chain, cycloalkyl with 5 to 14, preferably 8 to 12, ring carbon atoms, phenyl or benzyl, or N-methylolmelamines with 2 to 6, optionally partially etherified methylol groups, for example 1 to 5 methylol groups etherified with an alkanol having 1 to 22 carbon atoms, especially with methanol, butanol or octadecylalcohol, have proved particularly suitable.

The radical Z is derived, for example, from n-butanol, lauryl alcohol, stearyl alcohol, oleyl alcohol, behenyl alcohol, ricinol, cetyl alcohol, cyclohexanol, cyclododecanol, p-nonylcyclohexanol, hydroabietyl alcohol, benzyl alcohol or phenol.

Amongst the compounds of the formula (3), those of the formula

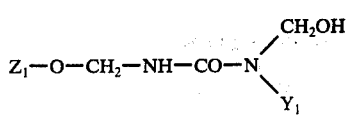 (4)

wherein $Y_1$ denotes hydrogen or methylol and $Z_1$ represents alkyl or alkenyl each with 4 to 18, preferably 10 to 18, carbon atoms, benzyl, a monoethylene glycol or polyethylene glycol radical with 1 to 25 ethoxy radicals in the chain or a monopropylene glycol or polypropylene glycol radical with 1 to 25 propoxy radicals in the chain are above all particularly suitable.

Typical representatives of components (a) which are suitable for the process according to the invention are, for example

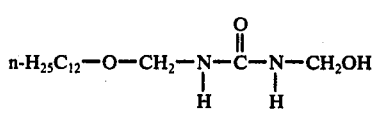 (5.1)
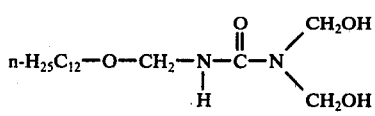 (5.2)
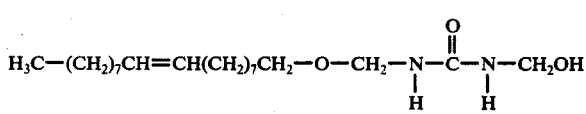 (5.3)
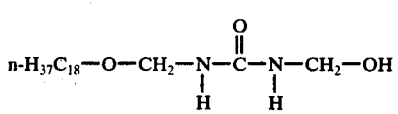 (5.4)
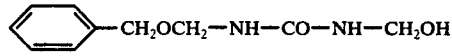 (5.5)
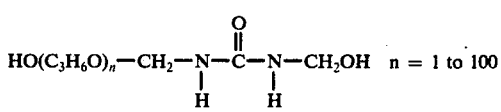 n = 1 to 100 (5.6)
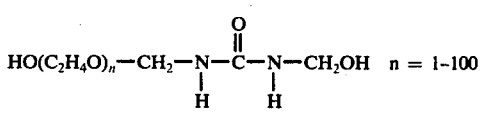 n = 1–100 (5.7)
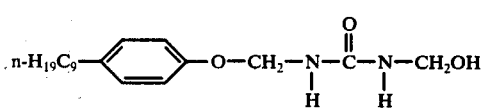 (5.8)
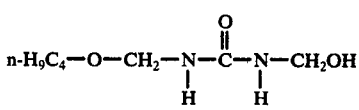 (5.9)
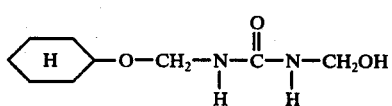 (5.10)
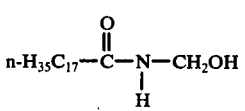 (6.1)
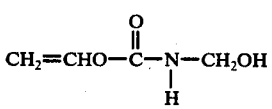 (6.2)
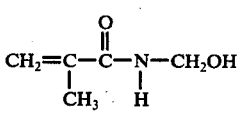 (6.3)
(6.4)

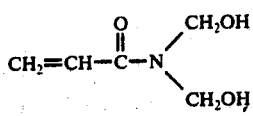
(6.5)

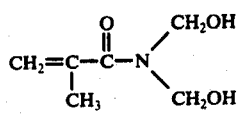
(7.1)

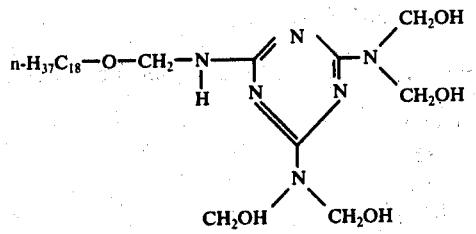
(7.2)

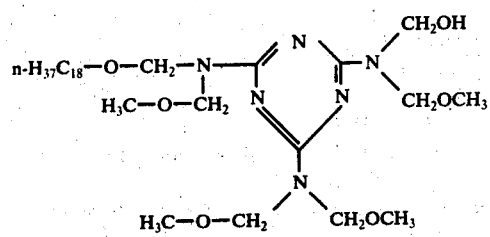
(7.3)

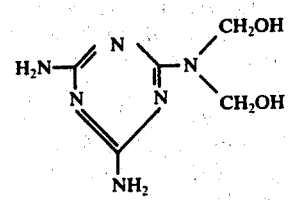
(7.4)

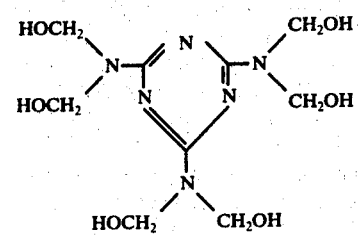
(7.5)

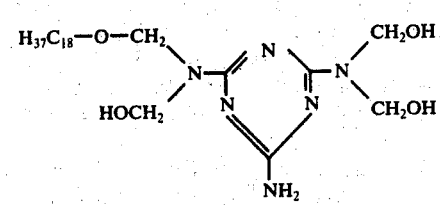

The component (b) is, for example, ethylene oxide, propylene oxide, styrene oxide or diglycidyl ether. Propylene oxide and above all ethylene oxide are preferred.

The component (c) is as a rule an alcoholate of transition metals of groups IV, V or VI of the 4th, 5th or 6th period of the periodic system according to "Lange's Handbook of Chemistry", 10th edition, 1967, pages 60 and 61. These transition metals, also called elements of the intermediate groups, of groups a or of groups b, include titanium, zirconium, hafnium, vanadium, niobium, tantalum, chromium, molybdenum and tungsten.

The process is appropriately carried out in the presence of metal alcoholates of the formula $$Me_1(O-X)_n \qquad (8)$$

wherein $Me_1$
denotes niobium$^V$, tantalum$^V$, tungsten$^{VI}$, molybdenum$^{VI}$, zirconium$^{IV}$ or hafnium$^{IV}$ and $n$ denotes 4, 5 or 6, depending on the valency of the metal, and X has the indicated meaning.

Preferred metal alcoholates correspond to the formula $$Me_2(O-X)_{n_1}' \quad (9)$$

wherein $Me_2$ denotes zirconium$^{IV}$, niobium$^V$, tantalum$^V$ tungsten$^{VI}$ and $n_1$ denotes 4, 5 or 6 and X has the indicated meaning, especially alkyl with 1 to 4 carbon atoms. Amongst these metal alcoholates, niobium alcoholates and tantalum alcoholates with 1 to 4 carbon atoms, for example tantalum ethylate and tantalum tert. butylate and niobium ethylate and niobium tert. butylate are particularly effective. The radical —O—X in the formulae (2), (8) and (9) is preferably a radical of an optionally chlorinated alkanol with up to 4 carbon atoms, such as, for example, methanol, ethanol, β-chloroethanol, isopropanol, n-propanol, n-butanol, sec.- or tert.-butanol, of a cycloalkanol with, appropriately, 5 to 12, or preferably 8 to 12, ring carbon atoms, such as cyclododecanol, or a radical of phenol or benzyl alcohol. As halogen, Q denotes, for example, bromine or preferably chlorine. As alkoxy, Q is as a rule different from OX and can, for example, be methoxy, ethoxy, propoxy, iso-propoxy, n-butoxy or, preferably, tert. butoxy. $r$ preferably has the same meaning as $n$, so that metal alcoholates of the formula $Me(OX)_n$ are preferred. The process according to the invention is preferably carried out in the presence of the optional additional component (d). Such components are, for example, alkali metal hydroxides, such as lithium hydroxide, sodium hydroxide, potassium hydroxide, rubidium hydroxide or caesium hydroxide or the corresponding alcoholates of alkanols with 1 to 4 carbon atoms, as indicated for the component (c).

Preferably, sodium hydroxide or potassium hydroxide or a sodium alcoholate or potassium alcoholate of an alkanol with 1 to 4 carbon atoms is used as the component (d).

Relative to the weight of the reaction mixture, 0.05 to 5%, preferably 0.1 to 2%, and especially 0.4 to 1%, of the catalysts(c) or (c) and (d) together are advantageously employed.

If the catalysts (c) and (d) are used together, the weight ratio of (c) to (d) is as a rule 9:1 to 1:9, preferably 4:1 to 1:4 or, above all, 7:3 to 3:7.

Typical representatives of the component (c) are, for example:

| | |
|---|---|
| $Ta(OCH_3)_5$ | (10.1) |
| $Ta(OC_2H_5)_5$ | (10.2) |
| $Ta(O\text{-}CH(CH_3)_2)_5$ | (10.3) |
| $Ta(OC(CH_3)_3)_5$ | (10.4) |

 (10.5)

| | |
|---|---|
| $Nb(OCH_3)_5$ | (10.6) |
| $Nb(OC_2H_5)_5$ | (10.7) |
| $Nb(O\text{-}CH(CH_3)_2)_5$ | (10.8) |
| $Nb(OC(CH_3)_3)_5$ | (10.9) |

 (10.10)

| | |
|---|---|
| $W(OCH_3)_6$ | (10.11) |
| $W(OC(CH_3)_3)_6$ | (10.12) |
| $Hf(O\text{—}CH(CH_3)_2)_4$ | (10.13) |
| $Hf(O\text{—}C(CH_3)_3)_4$ | (10.14) |
| $Mo(O\text{—}CH(CH_3)_2)_6$ | (10.15) |
| $Mo(O\text{—}C(CH_3)_3)_6$ | (10.16) |
| $Ti(OC_2H_5)_4$ | (10.17) |
| $Ti(O\text{—}C(CH_3)_3)_4$ | (10.18) |
| $Zr(OC_2H_5)_4$ | (10.19) |
| $Zr(O\text{—}C(CH_3)_3)_4$ | (10.20) |
| $Ta(OCH_3)Cl_4$ | (10.21) |
| $Nb(OCH_3)_4Cl$ | (10.22) |
| $Ti(OC_4H_9)_4$ | (10.23) |
| $ZrOCH_3(OC(CH_3)_3)_4$ | (10.24) |
| $Zr(OCH_3)Cl_3$ | (10.25) |

Typical representatives of the component (d) are, for example:

| | |
|---|---|
| LiOH | (11.1) |
| NaOH | (11.2) |
| KOH | (11.3) |
| $LiOCH_3$ | (11.4) |
| $NaOCH_3$ | (11.5) |
| $NaOC_2H_5$ | (11.6) |
| $NaOC(CH_3)_3$ | (11.7) |
| $KOCH_3$ | (11.8) |
| $KOC_2H_5$ | (11.9) |
| $KOC(CH_3)_3$ | (11.10) |

The reaction temperature is preferably 30° to 120° C or especially 40° to 90° C.

The reaction can be carried out at atmospheric pressure or at an excess pressure of up to 20 atmospheres gauge. Preferably, the pressure is 1 to 15 atmospheres gauge or especially 1 to 11 atmospheres gauge. As a rule, the reaction is carried out at the so-called autogenic pressure, that is to say the pressure generated by the reaction mixture itself, at the particular temperature.

Depending on the end use of the reaction products, 1 to 100, preferably 1 to 25, mols of the component (b) are as a rule added onto the component (a).

At times it can be appropriate to carry out the alkoxylation in the presence of a second alkoxide which does not participate in the actual reaction. For example it is possible to carry out the reaction with ethylene oxide and to use propylene oxide or dioxane as the reaction medium or as the suspension agent.

The process according to the invention has the advantage that alkylene oxides can be directly added onto a N-methylolated nitrogen compound under mild conditions, that is to say at relatively low temperatures and with a practically neutral catalyst system. It is known that N-methylol compounds are unstable in even a weakly acid medium and in a strongly alkaline medium form polycondensates or split off formaldehyde and water.

Addition reactions of, for example, ethylene oxide to an organic compound which possesses a mobile hydrogen atom are usually carried out at temperatures of 160° to 200° C. However, at such high temperatures most N-methylol compounds are no longer stable, that is to say a degradation of the methylol groups takes place. By means of the catalyst system used according to the invention (component (c) alone or (c) and (d) together) it has now become possible to carry out such addition reactions successfully even at relatively low temperatures, that is to say at temperatures below 160° C, without a degradation of the methylol groups taking place.

Because of their methylol groups or etherified methylol groups the products manufactured according to the process of the invention are reactive and can be used for various purposes, depending on the substitution. In particular, they are suitable for use as so-called reactive surface-active agents, that is to say as reactive surface-active products which under certain conditions, for example in an acid medium or at an elevated temperature, can be converted into an irreversibly insoluble state. They can be used, for example, for the manufacture of micro-capsules. Furthermore, such products are suitable for use as detergents, detergent additives, emulsifiers, dispersing agents, additives to agents which confirm hydrophobic properties, or as such agents themselves, agents for imparting a soft handle and hydrophilic properties, or carriers.

Asymmetrical diether compounds which possess at least one hydrophobic and hydrophilic radical, are in particular valuable reactive surface-active agents.

The introduction of the hydrophilic and hydrophobic groups can be carried out in optional sequence.

In the case of the asymmetrical ethers of dimethylolurea the procedure followed is, for example, first to etherify the monomethylolurea hydrophobically or hydrophilically. A second molecule of formaldehyde is then added onto the resulting monoethers of monomethylolurea, to form the monoether of dimethylolurea. This monoether is again etherified hydrophilically or hydrophobically so that an end product which contains both a hydrophilic and a hydrophobic ether group results.

The introduction of the hydrophilic groups which confer solubility in water is effected, for example, by reacting the monomethylol compound in question, in the presence of a catalyst, with, for example, ethylene oxide, whereby a polyethylene glycol ether is formed. The hydrophobic group is most simply introduced by direct etherification of the methylol group in a weakly acid medium with a hydroxyl compound contain 4 or more carbon atoms. It is optionally also possible first to carry out an etherification with a lower alcohol and to introduce the higher alcohol of low volatility by trans-etherification. A further possibility of introducing hydrophobic groups consists of the reaction of the free methylol groups with, for example, propylene oxide. Since a reaction with ethylene oxide is carried out in the preceding or subsequent stage, one obtains, for example, dimethylolurea which is etherified on one side with propylene oxide and on the other with a polyethylene glycol.

A preferred procedure is, for example, the following: The monomethylol compound of the urea, which is manufactured in a known manner by addition of one molecule of formaldehyde, is appropriately first etherified with n-butanol, and the ethers of the higher alcohols are manufactured by transetherification of the n-butyl-ether. n-Butanol is preferred because with it the reaction can be carried out in a homogeneous phase and during the trans-etherification the n-butanol can again be distilled off in vacuo at a temperature which is not excessively high. The latter point is important because in the etherification which takes place in a weakly acid medium, for example a medium containing acetic acid, some insoluble carbamide resin is always produced. When etherifying monomethylolurea with n-butanol it is advisable to etherify methylolureas containing at least 5% of water, that is to say not to dry them too thoroughly before the etherification. The addition of the ethylene oxide onto the methylol groups of the ureas is carried out in accordance with the process of the invention. The length of the polyglycol-ether chain plays an important role because it influences the solubility of this surface-active agent, especially the solubility in water.

The examples which follow explain the invention without restricting it thereto. In the examples, percentages are percentages by weight throughout.

EXAMPLE 1

100 mg of $Ta(OC(CH_3)_3)_5$, 6.6 g (corresponding to 8 mols) of ethylene oxide and 5.4 g of the compound of the formula (5.1) (1 mol) are sealed in a glass tube of 70 ml capacity. The mixture is allowed to react for 16 hours at a pressure of 10.5 atmospheres gauge, whilst shaking, in a heating bath thermostatically controlled to 90° C, in the course of which 99% of the ethylene oxide undergo addition. This accordingly yields an end product which predominantly corresponds to the formula

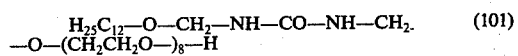
(101)

The infra-red spectrum of this product shows the following bands:

| | | | |
|---|---|---|---|
| Broad | band at approx. | 3,320 cm$^{-1}$ | strong |
| Sharp shoulder | " | 2,960 cm$^{-1}$ | strong-medium |
| Sharp | " | 2,920 cm$^{-1}$ | weak |
| Sharp | " | 2,840 cm$^{-1}$ | strong |
| Sharp shoulder | " | 1,710 cm$^{-1}$ | strong-medium |
| Sharp | " | 1,630 cm$^{-1}$ | medium |
| Sharp | " | 1,575 cm$^{-1}$ | weak |
| Broad shoulder | " | 1,555 cm$^{-1}$ | weak |
| Sharp shoulder | " | 1,500 cm$^{-1}$ | weak |
| Sharp | " | 1,460 cm$^{-1}$ | weak-medium |
| Sharp shoulder | " | 1,450 cm$^{-1}$ | weak-medium |
| Broad shoulder | " | 1,395 cm$^{-1}$ | weak |
| Sharp shoulder | " | 1,380 cm$^{-1}$ | weak |
| Sharp shoulder | " | 1,360 cm$^{-1}$ | weak |
| Broad shoulder | " | 1,300 cm$^{-1}$ | weak |
| Broad shoulder | " | 1,290 cm$^{-1}$ | weak |
| Broad | " | 1,250 cm$^{-1}$ | weak-medium |
| Broad | " | 1,075 cm$^{-1}$ | medium-strong |
| Broad | " | 1,045 cm$^{-1}$ | weak |
| Broad shoulder | " | 1,030 cm$^{-1}$ | medium |
| Sharp | " | 920 cm$^{-1}$ | weak |
| Broad | " | 880 cm$^{-1}$ | weak |
| Broad | " | 840 cm$^{-1}$ | weak |
| Sharp | " | 800 cm$^{-1}$ | weak |
| Sharp | " | 710 cm$^{-1}$ | weak-medium |
| Sharp shoulder | " | 660 cm$^{-1}$ | weak-medium |

EXAMPLE 2

100 mg of $Ta(OC(CH_3)_3)_5$, 11 g (corresponding to 5 mols) of ethylene oxide and 14.4 g (1 mol) of the compound of the formula (5.2) (urea-monomethylol-dodecyl-ether post-methylolated with paraformaldehyde) are sealed in a glass tube, as described in Example 1. This reaction mixture is left to react for 16 hours at a pressure of 17.5 atmospheres gauge, whilst shaking, in a heating bath thermostatically controlled to 110° C, in the course of which 98.7% of the ethylene oxide undergo addition. Hence, a reaction product which predominantly corresponds to the formula

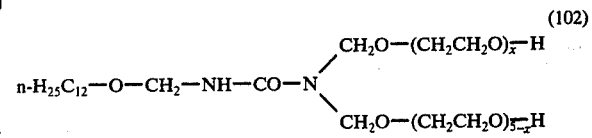
(102)

$x = 1 - 5$ is obtained.

The infra-red spectrum of this product shows the following bands:

| | | | |
|---|---|---|---|
| Broad | band at approx. | 3,400 cm$^{-1}$ | medium |
| Sharp shoulder | " | 2,940 cm$^{-1}$ | medium-strong |
| Sharp | " | 2,910 cm$^{-1}$ | weak |
| Sharp shoulder | " | 2,860 cm$^{-1}$ | weak |
| Sharp | " | 2,850 cm$^{-1}$ | strong |
| Broad shoulder | " | 2,730 cm$^{-1}$ | weak |
| Broad | " | 1,740 cm$^{-1}$ | weak-medium |
| Broad | " | 1,710 cm$^{-1}$ | weak |
| Broad shoulder | " | 1,660 cm$^{-1}$ | weak-medium |
| Sharp | " | 1,650 cm$^{-1}$ | weak |
| Sharp shoulder | " | 1,630 cm$^{-1}$ | medium |
| Sharp shoulder | " | 1,555 cm$^{-1}$ | weak |
| Sharp shoulder | " | 1,535 cm$^{-1}$ | weak |
| Sharp shoulder | " | 1,500 cm$^{-1}$ | weak |
| Sharp shoulder | " | 1,490 cm$^{-1}$ | weak |
| Broad | " | 1,455 cm$^{-1}$ | weak-medium |
| Broad shoulder | " | 1,370 cm$^{-1}$ | weak |
| Sharp | " | 1,340 cm$^{-1}$ | weak |
| Broad | " | 1,285 cm$^{-1}$ | weak |
| Broad | " | 1,240 cm$^{-1}$ | weak |
| Broad | " | 1,110 cm$^{-1}$ | medium |
| Broad shoulder | " | 1,070 cm$^{-1}$ | weak |
| Broad shoulder | " | 1,035 cm$^{-1}$ | weak-medium |
| Broad | " | 935 cm$^{-1}$ | weak |
| Broad | " | 880 cm$^{-1}$ | weak |
| Broad | " | 835 cm$^{-1}$ | weak |
| Sharp shoulder | " | 800 cm$^{-1}$ | weak |
| Broad | " | 750 cm$^{-1}$ | weak |
| Sharp shoulder | " | 710 cm$^{-1}$ | weak |
| Sharp shoulder | " | 650 cm$^{-1}$ | weak |

EXAMPLE 3

100 mg of a catalyst mixture of NaOC$_2$H$_5$ and Nb(OC(CH$_3$)$_3$)$_5$ [mixed in the ratio of 1:1], 6.6 g of ethylene oxide [corresponding to 6 mols] and 6.7g (1 mol) of the compound of the formula (5.3) are sealed in a glass tube, as described in Example 1. This reaction mixture is reacted for 16 hours at a pressure of 5.2 atmospheres gauge, whilst shaking, in a heating bath thermostatically controlled to 60° C, in the course of which 98% of the ethylene oxide employed undergo addition.

A reaction product which in the main corresponds to the formula

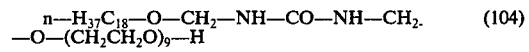

$$H_3C-(CH_2)_7-CH=CH-(CH_2)_7-CH_2-O- \quad (103)$$

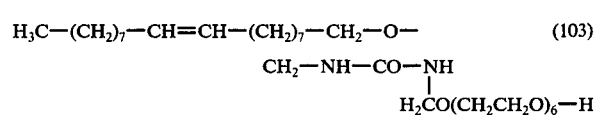

is obtained.

The infra-red spectrum of this product shows the following bands:

| | | | |
|---|---|---|---|
| Broad | band at approx. | 3,400 cm$^{-1}$ | medium |
| Broad shoulder | " | 2,990 cm$^{-1}$ | weak |
| Sharp | " | 2,910 cm$^{-1}$ | strong |
| Sharp shoulder | " | 2,860 cm$^{-1}$ | weak |
| Sharp | " | 2,840 cm$^{-1}$ | strong |
| Broad shoulder | " | 2,730 cm$^{-1}$ | weak |
| Broad | " | 1,760 cm$^{-1}$ | weak |
| Broad | " | 1,705 cm$^{-1}$ | weak |
| Broad | " | 1,650 cm$^{-1}$ | weak-medium |
| Broad shoulder | " | 1,630 cm$^{-1}$ | weak-medium |
| Sharp shoulder | " | 1,555 cm$^{-1}$ | weak |
| Broad shoulder | " | 1,535 cm$^{-1}$ | weak |
| Sharp shoulder | " | 1,500 cm$^{-1}$ | weak |
| Sharp | " | 1,490 cm$^{-1}$ | weak |
| Broad | " | 1,455 cm$^{-1}$ | weak-medium |
| Sharp shoulder | " | 1,370 cm$^{-1}$ | weak |
| Sharp | " | 1,340 cm$^{-1}$ | weak |
| Broad | " | 1,285 cm$^{-1}$ | weak |
| Broad | " | 1,240 cm$^{-1}$ | weak |
| Broad | " | 1,110 cm$^{-1}$ | strong |
| Broad shoulder | " | 1,065 cm$^{-1}$ | weak |
| Broad shoulder | " | 1,030 cm$^{-1}$ | weak-medium |
| Broad | " | 940 cm$^{-1}$ | weak |
| Sharp | " | 880 cm$^{-1}$ | weak |
| Broad | " | 835 cm$^{-1}$ | weak |
| Broad shoulder | " | 800 cm$^{-1}$ | weak |
| Sharp shoulder | " | 760 cm$^{-1}$ | weak |
| Sharp shoulder | " | 745 cm$^{-1}$ | weak |
| Broad shoulder | " | 715 cm$^{-1}$ | weak |
| Sharp shoulder | " | 655 cm$^{-1}$ | weak |

EXAMPLE 4

100 mg of a catalyst mixture of KOC$_2$H$_5$ and Nb(OC(CH$_3$)$_3$)$_5$ [in the ratio of 1:1] together with 9.9 g (9 mols) of ethylene oxide and 10.15 g (1 mol) of the compound of the formula (5.4) are sealed in a glass tube, as described in Example 1. This mixture is reacted for 16 hours at a pressure of 5.2 atmospheres gauge and whilst shaking, in a heating bath thermostatically controlled to 60° C, in the course of which 99.4% of the ethylene oxide undergo addition. A reaction product which predominantly corresponds to the formula $$n-H_{37}C_{18}-O-CH_2-NH-CO-NH-CH_2-O-(CH_2CH_2O)_9-H \quad (104)$$

is obtained.

The infra-red spectrum of this product shows the following bands:

| | | | |
|---|---|---|---|
| Broad shoulder | band at approx. | 3,420 cm$^{-1}$ | medium |
| Broad | " | 3,350 cm$^{-1}$ | medium |
| Sharp shoulder | " | 2,960 cm$^{-1}$ | medium-strong |
| Sharp | " | 2,920 cm$^{-1}$ | weak |
| Sharp | " | 2,850 cm$^{-1}$ | strong |
| Broad shoulder | " | 2,740 cm$^{-1}$ | weak |
| Broad shoulder | " | 1,730 cm$^{-1}$ | weak |
| Sharp shoulder | " | 1,700 cm$^{-1}$ | weak |
| Broad | " | 1,650 cm$^{-1}$ | medium |
| Broad shoulder | " | 1,625 cm$^{-1}$ | weak |
| Sharp shoulder | " | 1,555 cm$^{-1}$ | weak |
| Sharp shoulder | " | 1,535 cm$^{-1}$ | weak |
| Sharp | " | 1,460 cm$^{-1}$ | weak-medium |
| Broad shoulder | " | 1,375 cm$^{-1}$ | weak |
| Sharp | " | 1,345 cm$^{-1}$ | weak |
| Sharp shoulder | " | 1,320 cm$^{-1}$ | weak |
| Broad | " | 1,290 cm$^{-1}$ | weak |
| Broad | " | 1,245 cm$^{-1}$ | weak-medium |
| Broad | " | 1,110 cm$^{-1}$ | medium-strong |
| Broad shoulder | " | 1,070 cm$^{-1}$ | weak |
| Broad shoulder | " | 1,035 cm$^{-1}$ | weak-medium |
| Broad | " | 940 cm$^{-1}$ | weak |
| Broad | " | 885 cm$^{-1}$ | weak |
| Broad shoulder | " | 840 cm$^{-1}$ | weak |
| Sharp | " | 750 cm$^{-1}$ | weak |
| Sharp | " | 720 cm$^{-1}$ | weak |
| Sharp shoulder | " | 660 cm$^{-1}$ | weak |

EXAMPLE 5

100 mg of a catalyst mixture of Ta(OC(CH$_3$)$_3$)$_5$ and NaOC$_2$H$_5$ [in the ratio of 1:1], 8.8 g of ethylene oxide [corresponding to 4 mols] and 5.4 g of the compound of the formula (5.5) are sealed in a glass tube. This mixture is reacted for 16 hours at a pressure of 5.2 atmospheres gauge and whilst shaking, in a heating bath thermostatically controlled to 60°, in the course of which 97% of the ethylene oxide undergo addition.

A reaction product of the formula

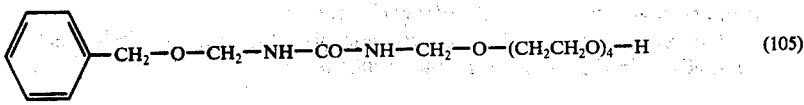   (105)

is obtained.

The infra-red spectrum of this product shows the following bands:

| | | | |
|---|---|---|---|
| Broad shoulder | band at approx. | 3,420 cm$^{-1}$ | medium |
| Broad | " | 3,340 cm$^{-1}$ | medium |
| Broad | " | 2,920 cm$^{-1}$ | medium-strong |
| Sharp | " | 2,870 cm$^{-1}$ | medium-strong |
| Broad shoulder | " | 2,740 cm$^{-1}$ | weak |
| Broad shoulder | " | 1,740 cm$^{-1}$ | weak |
| Sharp | " | 1,705 cm$^{-1}$ | weak |
| Broad shoulder | " | 1,650 cm$^{-1}$ | weak-medium |
| Broad | " | 1,635 cm$^{-1}$ | weak-medium |
| Sharp shoulder | " | 1,560 cm$^{-1}$ | weak |
| Sharp | " | 1,540 cm$^{-1}$ | weak |
| Sharp shoulder | " | 1,510 cm$^{-1}$ | weak |
| Sharp shoulder | " | 1,500 cm$^{-1}$ | weak |
| Broad | " | 1,455 cm$^{-1}$ | weak |
| Broad shoulder | " | 1,440 cm$^{-1}$ | weak |
| Broad shoulder | " | 1,380 cm$^{-1}$ | weak |
| Sharp | " | 1,350 cm$^{-1}$ | weak |
| Broad | " | 1,295 cm$^{-1}$ | weak |
| Broad | " | 1,250 cm$^{-1}$ | weak |
| Broad shoulder | " | 1,220 cm$^{-1}$ | weak |
| Broad | " | 1,110 cm$^{-1}$ | medium-strong |
| Broad shoulder | " | 1,070 cm$^{-1}$ | weak |
| Broad shoulder | " | 1,040 cm$^{-1}$ | medium |
| Broad | " | 940 cm$^{-1}$ | weak |
| Sharp | " | 885 cm$^{-1}$ | weak |
| Broad shoulder | " | 805 cm$^{-1}$ | weak |
| Broad | " | 745 cm$^{-1}$ | weak |
| Sharp | " | 700 cm$^{-1}$ | weak |
| Sharp shoulder | " | 660 cm$^{-1}$ | weak |

EXAMPLE 6

100 mg of Ta(OC$_2$H$_5$)$_5$, 13.2 g of ethylene oxide (corresponding to 15 mols) and 10 g (1 mol) of the compound of the formula (7.2) are sealed in a glass tube and reacted for 16 hours at a pressure of 10.5 atmospheres gauge and whilst shaking, in a heating bath thermostatically controlled to 90° C, in the course of which 100% of the ethylene oxide undergo addition.

A reaction product which predominantly corresponds to the formula

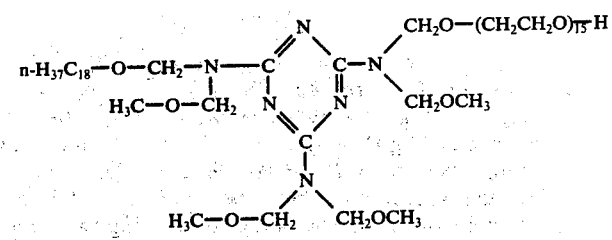

(106)

is obtained.

The infra-red spectrum of this product shows the following bands:

| | | | |
|---|---|---|---|
| Broad | band at approx. | 3,430 cm$^{-1}$ | weak |
| Sharp shoulder | " | 2,970 cm$^{-1}$ | weak-medium |
| Broad | " | 2,900 cm$^{-1}$ | strong |
| Broad shoulder | " | 2,850 cm$^{-1}$ | strong |
| Broad shoulder | " | 2,740 cm$^{-1}$ | weak |
| Broad | " | 2,460 cm$^{-1}$ | weak |
| Broad | " | 1,710 cm$^{-1}$ | weak |
| Sharp | " | 1,540 cm$^{-1}$ | strong |
| Sharp shoulder | " | 1,470 cm$^{-1}$ | medium |
| Broad shoulder | " | 1,450 cm$^{-1}$ | weak |
| Broad shoulder | " | 1,430 cm$^{-1}$ | weak-medium |
| Sharp | " | 1,370 cm$^{-1}$ | weak-medium |
| Sharp | " | 1,340 cm$^{-1}$ | weak |
| Sharp | " | 1,320 cm$^{-1}$ | weak |
| Sharp | " | 1,290 cm$^{-1}$ | weak |
| Broad shoulder | " | 1,125 cm$^{-1}$ | medium |
| Broad | " | 1,085 cm$^{-1}$ | weak-medium |
| Broad shoulder | " | 1,030 cm$^{-1}$ | medium |
| Sharp | " | 940 cm$^{-1}$ | weak |
| Sharp | " | 900 cm$^{-1}$ | weak |
| Broad | " | 850 cm$^{-1}$ | weak-medium |

EXAMPLE 7

100 mg of a catalyst mixture of NaOH and Nb(OC(CH$_3$)$_3$)$_5$ [in the ratio of 1:1], 3.5 g of ethylene oxide (corresponding to 3 mols) of 7.6 g (1 mol) of the compound of the formula (6.1) are sealed in a glass tube. This mixture is reacted for 16 hours at a pressure of 5.2 atmospheres gauge, whilst shaking, in a heating bath thermostatically controlled to 60° C, in the course of which 75% of the ethylene oxide undergo addition. The reaction product in the main corresponds to the formula $$\text{n--H}_{35}\text{C}_{17}\text{--CO--NH--CH}_2\text{O--(CH}_2\text{CH}_2\text{O)}_3\text{--H} \quad (107)$$

The infra-red spectrum of this product shows the following bands:

| | | | |
|---|---|---|---|
| Broad | band at approx. | 3,650 cm$^{-1}$ | weak |
| Broad shoulder | " | 3,560 cm$^{-1}$ | weak |
| Sharp | " | 3,420 cm$^{-1}$ | medium |
| Broad shoulder | " | 3,350 cm$^{-1}$ | medium |
| Broad shoulder | " | 2,970 cm$^{-1}$ | weak-medium |
| Broad | " | 2,910 cm$^{-1}$ | strong |
| Sharp | " | 2,840 cm$^{-1}$ | strong |
| Broad shoulder | " | 2,720 cm$^{-1}$ | weak |
| Broad | " | 2,460 cm$^{-1}$ | weak |
| Broad shoulder | " | 1,710 cm$^{-1}$ | weak |
| Broad | " | 1,665 cm$^{-1}$ | strong |
| Broad | " | 1,585 cm$^{-1}$ | weak |
| Broad shoulder | " | 1,530 cm$^{-1}$ | weak |
| Sharp | " | 1,490 cm$^{-1}$ | weak |
| Sharp | " | 1,450 cm$^{-1}$ | weak-medium |
| Broad shoulder | " | 1,410 cm$^{-1}$ | weak |
| Broad shoulder | " | 1,360 cm$^{-1}$ | weak |
| Sharp | " | 1,340 cm$^{-1}$ | weak |
| Broad shoulder | " | 1,110 cm$^{-1}$ | medium-strong |
| Broad | " | 1,065 cm$^{-1}$ | weak |
| Broad shoulder | " | 1,035 cm$^{-1}$ | medium-strong |
| Broad | " | 925 cm$^{-1}$ | weak |
| Sharp | " | 875 cm$^{-1}$ | weak |

EXAMPLE 8

100 mg of Ta(OC(CH$_3$)$_3$)$_5$, 13.2 g of ethylene oxide (corresponding to 6 mols) and 9.3 g (1 mol) of the compound of the formula (7.3) are sealed in a glass tube. This reaction mixture is reacted for 16 hours at a pressure of 5.2 atmospheres gauge and whilst shaking, in a heating bath thermostatically controlled at 60° C, in the course of which 100% of the ethylene oxide undergo addition. A reaction product which predominantly corresponds to the formula

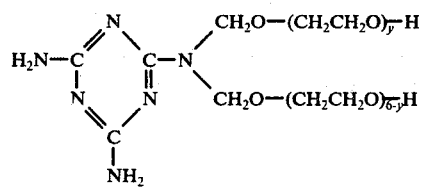

$y = 1$ to 6 is obtained.

The infra-red spectrum of this product shows the following bands:

| Broad shoulder | band at approx. | 3,400 cm$^{-1}$ | strong-medium |
|---|---|---|---|
| Broad shoulder | " | 3,350 cm$^{-1}$ | strong-medium |
| Sharp shoulder | " | 2,940 cm$^{-1}$ | strong-medium |
| Broad shoulder | " | 2,910 cm$^{-1}$ | weak |
| Sharp | " | 2,860 cm$^{-1}$ | strong |
| Broad shoulder | " | 2,740 cm$^{-1}$ | weak |
| Broad shoulder | " | 1,730 cm$^{-1}$ | weak |
| Broad shoulder | " | 1,630 cm$^{-1}$ | medium |
| Broad shoulder | " | 1,570 cm$^{-1}$ | weak-medium |
| Broad | " | 1,550 cm$^{-1}$ | weak |
| Broad | " | 1,500 cm$^{-1}$ | weak |
| Broad | " | 1,455 cm$^{-1}$ | weak-medium |
| Sharp | " | 1,345 cm$^{-1}$ | weak-medium |
| Broad | " | 1,320 cm$^{-1}$ | weak |
| Broad | " | 1,290 cm$^{-1}$ | weak |
| Sharp | " | 1,240 cm$^{-1}$ | weak-medium |
| Broad | " | 1,100 cm$^{-1}$ | medium-strong |
| Broad shoulder | " | 1,070 cm$^{-1}$ | weak |
| Broad shoulder | " | 1,035 cm$^{-1}$ | medium |
| Broad | " | 940 cm$^{-1}$ | weak-medium |
| Sharp | " | 880 cm$^{-1}$ | weak |
| Broad | " | 840 cm$^{-1}$ | weak |
| Sharp | " | 810 cm$^{-1}$ | weak-medium |
| Broad shoulder | " | 740 cm$^{-1}$ | weak |
| Sharp shoulder | " | 655 cm$^{-1}$ | weak-medium |

EXAMPLE 9

100 mg of Ta(OC$_2$H$_5$)$_5$, 11 g of ethylene oxide (corresponding to 5 mols) and a mixture of 7.5 g (1 mol) of the compound of the formula (7.4) in 7.2 g of propylene oxide (as a suspending agent which can easily be removed again) are sealed in a glass tube. This mixture is reacted for 16 hours at a pressure of 10.5 atmospheres gauge and whilst shaking, in a heating bath thermostatically controlled to 90° C. After removing the propylene oxide, which has not participated in the reaction, it is possible to ascertain that 100% of the ethylene oxide have undergone addition.

Hence, a reaction product which predominantly corresponds to the formula

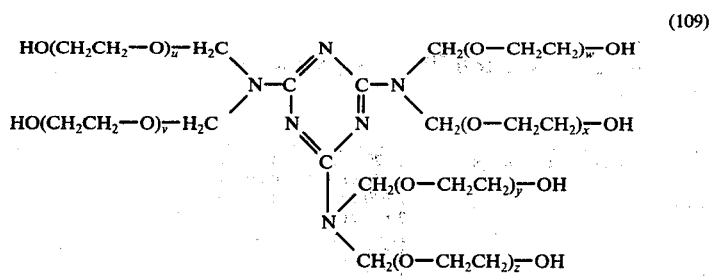

$u + v + w + x + y + z = 5$ is obtained.

The infra-red spectrum of this product shows the following bands:

| Broad | band at approx. | 3,650 cm$^{-1}$ | weak |
|---|---|---|---|
| Sharp shoulder | " | 3,580 cm$^{-1}$ | medium |
| Broad | " | 3,480 cm$^{-1}$ | medium-strong |
| Sharp shoulder | " | 2,980 cm$^{-1}$ | medium |
| Sharp | " | 2,920 cm$^{-1}$ | medium |
| Sharp | " | 2,860 cm$^{-1}$ | medium-strong |
| Sharp shoulder | " | 2,800 cm$^{-1}$ | weak |
| Sharp shoulder | " | 2,780 cm$^{-1}$ | weak-medium |
| Broad | " | 2,460 cm$^{-1}$ | weak-medium |
| Broad shoulder | " | 1,785 cm$^{-1}$ | weak |
| Broad shoulder | " | 1,745 cm$^{-1}$ | weak |
| Sharp shoulder | " | 1,720 cm$^{-1}$ | weak |
| Broad | " | 1,660 cm$^{-1}$ | strong |
| Broad shoulder | " | 1,620 cm$^{-1}$ | weak |
| Broad shoulder | " | 1,580 cm$^{-1}$ | weak-medium |
| Broad | " | 1,545 cm$^{-1}$ | weak-medium |
| Broad | " | 1,480 cm$^{-1}$ | weak-medium |
| Broad shoulder | " | 1,450 cm$^{-1}$ | weak |
| Broad shoulder | " | 1,435 cm$^{-1}$ | weak |
| Sharp shoulder | " | 1,400 cm$^{-1}$ | weak |
| Sharp | " | 1,380 cm$^{-1}$ | weak-medium |
| Broad shoulder | " | 1,325 cm$^{-1}$ | weak |
| Broad shoulder | " | 1,140 cm$^{-1}$ | weak-medium |
| Sharp | " | 1,085 cm$^{-1}$ | medium |
| Broad shoulder | " | 1,040 cm$^{-1}$ | medium |
| Sharp | " | 965 cm$^{-1}$ | weak |
| Broad shoulder | " | 940 cm$^{-1}$ | weak |
| Sharp shoulder | " | 905 cm$^{-1}$ | weak |
| Broad shoulder | " | 880 cm$^{-1}$ | weak |
| Sharp | " | 860 cm$^{-1}$ | weak |

EXAMPLE 10

100 mg of a catalyst mixture of KOC$_2$H$_5$ and Nb(OC(CH$_3$)$_3$)$_5$ or Ta(OC(CH$_3$)$_3$)$_5$ [in the ratio of 1:1] and 3.5 g of ethylene oxide (corresponding to 4 mols) and 14 g (1 mol) of the compound of the formula (5.6), wherein $n = 18$, are sealed in a glass tube. This mixture is reacted for 16 hours at a pressure of 5.2 atmospheres gauge, whilst shaking, in a heating bath thermostatically controlled to 60° C, in the course of which 100% of the ethylene oxide undergo addition. A reaction product which predominantly corresponds to the formula

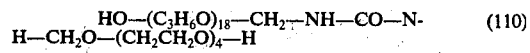

is obtained.

The starting product of the formula (5.6) can be obtained, for example, if 100 mg of catalyst mixture of KOC$_2$H$_5$ and potassium metal (in the ratio of 1:1), a mixture of 26 g of propylene oxide (corresponding to 18 mols) and 1.0 g of ethylene oxide (as the starter) and 2.25 g (1 mol) of monomethylolurea are sealed in a glass tube. This mixture is reacted for 16 hours at a pressure of 5.3 atmospheres gauge and whilst shaking, in a heating bath thermostatically controlled to 90° C, in the course of which 100% of the propylene oxide undergo addition. Instead of the above catalyst mixture, a mixture of KOC$_2$H$_5$ and Ta(OC$_2$H$_5$)$_5$ (in the ratio of 1:1) can also be used. This reaction product is thereafter subjected to a post-methylolation with paraformaldehyde. The infra-red spectrum of the product (110) shows the following bands:

| Broad | band at approx. | 3,360 cm$^{-1}$ | strong-medium |
|---|---|---|---|
| Sharp shoulder | " | 2,950 cm$^{-1}$ | medium |
| Broad shoulder | " | 2,910 cm$^{-1}$ | weak |
| Sharp shoulder | " | 2,860 cm$^{-1}$ | medium |
| Broad shoulder | " | 2,720 cm$^{-1}$ | weak |
| Sharp shoulder | " | 1,730 cm$^{-1}$ | weak-medium |
| Broad shoulder | " | 1,715 cm$^{-1}$ | weak |
| Sharp shoulder | " | 1,650 cm$^{-1}$ | weak |
| Sharp | " | 1,590 cm$^{-1}$ | weak-medium |
| Broad | " | 1,450 cm$^{-1}$ | weak-medium |
| Broad shoulder | " | 1,400 cm$^{-1}$ | weak |
| Sharp | " | 1,370 cm$^{-1}$ | weak |
| Broad shoulder | " | 1,355 cm$^{-1}$ | weak |
| Broad shoulder | " | 1,275 cm$^{-1}$ | weak |
| Broad | " | 1,235 cm$^{-1}$ | weak |
| Broad shoulder | " | 1,160 cm$^{-1}$ | weak-medium |
| Broad | " | 1,110 cm$^{-1}$ | medium |
| Broad shoulder | " | 1,075 cm$^{-1}$ | weak |
| Broad | " | 1,035 cm$^{-1}$ | weak |
| Sharp | " | 980 cm$^{-1}$ | weak-medium |
| Broad shoulder | " | 930 cm$^{-1}$ | weak-medium |
| Sharp | " | 880 cm$^{-1}$ | weak |
| Broad | " | 830 cm$^{-1}$ | weak |
| Sharp shoulder | " | 660 cm$^{-1}$ | weak-medium |

EXAMPLE 11

100 mg of a catalyst mixture of KOC(CH$_3$)$_3$ and Ta(OC$_2$H$_5$)$_5$ [in the ratio of 1:1], 13.2 g (corresponding to 6 mols) of ethylene oxide and 4.5 g (1 mol) of monomethylolurea are sealed in a glass tube. This mixture is reacted for 2 hours at a pressure of 1 - 2 atmospheres gauge and whilst shaking, in a heating bath which is initially kept at room temperature (20° to 25° C). Thereafter the heating bath is thermostatically controlled to 60° C and the reaction is continued for 16 hours at 5.2 atmospheres gauge, in the course of which 88% of the ethylene oxide undergo addition.

b. The reaction product described under (a) is subjected to a post-methylolation with paraformaldehyde and thereafter propylene oxide is added as follows onto this subsequently introduced methylol group.

100 mg of a catalyst mixture of (KOC$_2$H$_5$) and Ta(OC(CH$_3$)$_3$)$_5$ [in the ratio of 1:1], 8.7 g (corresponding to 6 mols) of propylene oxide and 9.6 g (1 mol) of the product of the formula (5.7) described under a), wherein $n = 6$, are sealed in a glass tube. This mixture is reacted, whilst shaking, in a thermostatically controlled heating bath, in accordance with the following programme: 2 hours at 25° C and 0.7 atmospheres gauge, 4 hours at 60° C and 2.5 atmospheres gauge and 16 hours at 110° C and 7.9 atmospheres gauge, in the course of which 100% of the propylene oxide undergo addition.

In the main, a reaction product of the formula

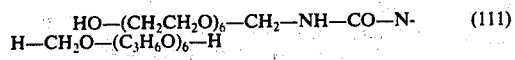

HO—(CH$_2$CH$_2$O)$_6$—CH$_2$—NH—CO—N-  (111)
H—CH$_2$O—(C$_3$H$_6$O)$_6$—H is obtained.

The infra-red spectrum of this product shows the following bands:

| Broad | band at approx. | 3,430 cm$^{-1}$ | medium |
|---|---|---|---|
| Sharp | " | 2,960 cm$^{-1}$ | medium-strong |
| Sharp shoulder | " | 2,910 cm$^{-1}$ | weak |
| Sharp | " | 2,860 cm$^{-1}$ | strong |
| Broad | " | 1,730 cm$^{-1}$ | weak |
| Broad shoulder | " | 1,705 cm$^{-1}$ | weak |
| Broad | " | 1,645 cm$^{-1}$ | weak |
| Broad shoulder | " | 1,500 cm$^{-1}$ | weak |
| Broad | " | 1,445 cm$^{-1}$ | weak-medium |
| Sharp | " | 1,365 cm$^{-1}$ | weak |
| Sharp | " | 1,340 cm$^{-1}$ | weak |
| Sharp | " | 1,315 cm$^{-1}$ | weak |
| Broad shoulder | " | 1,280 cm$^{-1}$ | weak |
| Broad | " | 1,250 cm$^{-1}$ | weak |
| Broad | " | 1,100 cm$^{-1}$ | strong |
| Broad | " | 1,030 cm$^{-1}$ | weak-medium |
| Broad shoulder | " | 990 cm$^{-1}$ | weak |
| Broad | " | 945 cm$^{-1}$ | weak-medium |
| Broad | " | 835 cm$^{-1}$ | weak |
| Broad shoulder | " | 740 cm$^{-1}$ | weak |
| Sharp shoulder | " | 655 cm$^{-1}$ | weak-medium |

EXAMPLE 12

100 mg of W(OC(CH$_3$)$_3$)$_6$, 6.6 g (0.15 mol) of ethylene oxide and 8.6 g (0.03 mol) of the compound of the formula (5.1) are sealed in a glass tube. The mixture is allowed to react for 16 hours at a pressure of 4.27 atmospheres gauge and whilst shaking, in a heating bath thermostatically controlled to 60° C, in the course of which 99% of the ethylene oxide undergo addition. An end product which predominantly corresponds to the formula

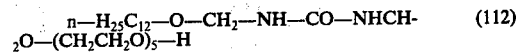

n—H$_{25}$C$_{12}$—O—CH$_2$—NH—CO—NHCH$_2$O—(CH$_2$CH$_2$O)$_5$—H  (112)

is obtained.

The infra-red spectrum of this product shows the following bands:

| Broad shoulder | band at approx. | 3,400 cm$^{-1}$ | strong-medium |
|---|---|---|---|
| Broad | " | 3,330 cm$^{-1}$ | medium-strong |
| Sharp shoulder | " | 2,950 cm$^{-1}$ | strong-medium |
| Sharp | " | 2,910 cm$^{-1}$ | weak |
| Sharp | " | 2,850 cm$^{-1}$ | strong |
| Broad shoulder | " | 2,740 cm$^{-1}$ | weak |
| Broad shoulder | " | 1,725 cm$^{-1}$ | weak |
| Broad | " | 1,635 cm$^{-1}$ | strong-medium |
| Broad | " | 1,530 cm$^{-1}$ | weak |
| Broad | " | 1,490 cm$^{-1}$ | weak |
| Broad | " | 1,450 cm$^{-1}$ | weak |
| Broad shoulder | " | 1,435 cm$^{-1}$ | weak |
| Sharp | " | 1,365 cm$^{-1}$ | weak |
| Sharp | " | 1,340 cm$^{-1}$ | weak |
| Broad shoulder | " | 1,280 cm$^{-1}$ | weak |
| Broad shoulder | " | 1,240 cm$^{-1}$ | weak |
| Broad shoulder | " | 1,170 cm$^{-1}$ | weak |
| Broad shoulder | " | 1,110 cm$^{-1}$ | medium |
| Broad shoulder | " | 1,060 cm$^{-1}$ | weak |
| Broad shoulder | " | 1,030 cm$^{-1}$ | medium |
| Broad | " | 935 cm$^{-1}$ | weak |
| Sharp | " | 880 cm$^{-1}$ | weak |
| Broad | " | 835 cm$^{-1}$ | weak |
| Broad shoulder | " | 800 cm$^{-1}$ | weak |
| Broad | " | 765 cm$^{-1}$ | weak |
| Broad | " | 745 cm$^{-1}$ | weak |
| Sharp | " | 710 cm$^{-1}$ | weak |
| Broad shoulder | " | 660 cm$^{-1}$ | weak |

EXAMPLE 13

100 mg of Ta(On-C$_3$H$_7$)$_5$, 7.92 g (corresponding to 6 mols) of ethylene oxide and 8.64 g (1 mol) of the compound of the formula (5.1) are sealed in a glass tube of 70 ml capacity. The mixture is allowed to react for 16 hours at a pressure of 10.5 atmospheres gauge and whilst shaking, in a heating bath thermostatically controlled to 90° C, in the course of which 95.2% of the ethylene oxide undergo addition. A highly viscous clear end product is obtained, which predominantly corresponds to the formula $$H_{25}C_{12}-O-CH_2-NH-CO-NH-CH_2O(CH_2CH_2O)_6-H \quad (113)$$

If, in this example, instead of 100 mg of Ta(On-C$_3$H$_7$)$_5$ the same amount of one of the following catalysts is employed, the same end product is obtained, with corresponding yields shown below.

| Example | Catalyst | Yield in % |
|---|---|---|
| 14 | Ta(O–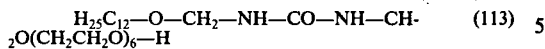)$_5$ | 97 |
| 15 | Ta(On—C$_5$H$_{11}$)$_5$ | 95.2 |
| 16 | Ta(OC(CH$_3$)$_3$)Cl$_4$ | 97.6 |
| 17 | Ta(O—cyclododecane)$_5$ | 98.1 |
| 18 | Nb(On—C$_9$H$_{19}$)$_5$ | 95.2 |
| 19 | | 96.5 |
| | Nb(O–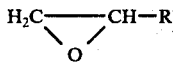)$_5$ | |
| 20 | | 92.8 |
| | Nb(O–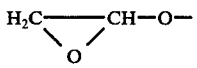)$_5$ | |
| 21 | Nb(O-cyclododecane)$_5$ | 95.2 |
| 22 | Nb(OCH[CH$_3$]$_2$)$_4$Cl | 97.6 |
| 23 | Nb(OCH[CH$_3$]$_2$)Cl$_4$ | 97.0 |
| 24 | Nb(O—CH[CH$_3$]$_2$)$_5$ | 95.8 |
| 25 | W(OC[CH$_3$]$_3$)$_6$ | 81.0 |
| 26 | Zr(On—C$_4$H$_9$)$_4$ | 99.0 |
| 27 | Zr(OC[CH$_3$]$_3$)$_4$ | 95.2 |
| 28 | Zr(OCH$_3$)Cl$_3$ | 96.4 |
| 29 | Zr(OC$_2$H$_4$Cl)$_4$ | 97.6 |
| 30 | Ti(On—C$_3$H$_7$)$_4$ | 97.0 |

We claim:

1. A process for the manufacture of alkoxylated N-methylol compound, which comprises reacting, at a temperature of 10° to 160° C and a pressure of 1 to 20 atmospheres gauge, (a) a N-methylolated urea with at most 22 carbon atoms with (b) an alkylene oxide of the formula $$H_2C\underset{O}{\overset{}{\diagdown\diagup}}CH-R$$

wherein R denotes hydrogen, alkyl with 1 to 3 carbon atoms, phenyl or a $$H_2C\underset{O}{\overset{}{\diagdown\diagup}}CH-O-$$

radical, in the presence of a catalytic amount of (c) at least one metal alcoholate of the formula $$Me(O-X)_r(Q)_{n-r}$$

wherein Me denotes a n-valent transition metal of groups IVB, VB, and VIB of the periodic system, X denotes alkyl with 1 to 4 carbon atoms, halogenoalkyl with 2 to 4 carbon atoms, phenyl, benzyl or cycloalkyl with at most 12 ring carbon atoms, Q denotes halogen or alkoxy with 1 to 4 carbon atoms, r denotes 1 to n and n denotes 4, 5 or 6, or in the presence of said component (c) together with (d) at least one alkali metal hydroxide or one alkali metal alcoholate of an alkanol with 1 to 4 carbon atoms.

2. A process as defined in claim 1, wherein, a compound of the formula $$Z-O-CH_2-NH-CO-N\underset{Y}{\overset{CH_2OH}{\diagup\diagdown}}$$

wherein Y denotes hydrogen, alkyl with 1 to 4 carbon atoms or methylol and Z denotes alkyl with 1 to 22 carbon atoms, alkenyl with 3 to 22 carbon atoms, a monoalkylene glycol or polyalkylene glycol radical with 2 or 3 carbon atoms per alkylene unit and with up to 100 alkoxy groups in the chain, cycloalkyl with 5 to 14 ring carbon atoms, phenyl or benzyl, is used as the component (a).

3. A process as defined in claim 1, wherein ethylene oxide, propylene oxide, diglycidyl-ether or styrene oxide is used as the component (b).

4. A process as defined in claim 3, wherein ethylene oxide is used as the component (b).

5. A process as defined in claim 1, wherein at least one metal alcoholate of the formula $$Me(OX')_n$$

wherein Me and n have the meaning indicated in claim 1 and X' denotes alkyl with 1 to 4 carbon atoms, phenyl, benzyl or cycloalkyl with at most 12 ring carbon atoms, is used as the component (c).

6. A process as defined in claim 1, wherein at least one metal alcoholate of the formula $$Me_1(O-X)_n$$

wherein Me$_1$ denotes niobium$^V$, tantalum$^V$, tungsten$^{VI}$, molybdenum$^{VI}$, zirconium$^{IV}$ or hafnium$^{IV}$ and n denotes 4, 5 or 6, corresponding to the valency of the metal, and X has the meaning indicated in claim 1, is used as the component (c).

7. A process as defined in claim 6, wherein at least one metal alcoholate of the formula $$Me_2(O-X)_{n_1}'$$

wherein Me$_2$ denotes zirconium$^{IV}$, niobium$^V$, tantalum$^V$ or tungsten$^{VI}$ and n$_1$ denotes 4, 5 or 6, and X represents alkyl with 1 to 4 carbon atoms, is used.

8. A process as defined in claim 1, wherein sodium hydroxide or potassium hydroxide or a sodium alcoholate or a potassium alcoholate of an alkanol with 1 to 4 carbon atoms, is used as component (d).

9. A process as defined in claim 1, wherein the reaction is carried out at 30° to 120° C.

10. A process as defined in claim 9, wherein the reaction is carried out at 40° to 90° C.

11. A process as defined in claim 1, wherein the reaction is carried out at a pressure of 1 to 11 atmospheres gauge.

12. A process as defined in claim 1, wherein 0.05 to 5%, preferably 0.1 to 2%, relative to the weight of the reaction mixture, of the components (c) and (d) together are employed.

13. A process as defined in claim 12, wherein the components (c) and (d) are employed in a weight ratio to one another of 9:1 to 1:9, preferably 4:1 to 1:4.

* * * * *